(12) United States Patent
Blanchette

(10) Patent No.: US 12,303,372 B2
(45) Date of Patent: May 20, 2025

(54) METHOD AND APPARATUS FOR STORING A FEMININE HYGIENE ARTICLE

(71) Applicant: Arrie Annie Blanchette, Harpers Ferry, WV (US)

(72) Inventor: Arrie Annie Blanchette, Harpers Ferry, WV (US)

( * ) Notice: Subject to any disclaimer, the term of this patent is extended or adjusted under 35 U.S.C. 154(b) by 846 days.

(21) Appl. No.: 16/533,288

(22) Filed: Aug. 6, 2019

(65) Prior Publication Data

US 2019/0358098 A1   Nov. 28, 2019

(51) Int. Cl.
*A61F 13/551* (2006.01)

(52) U.S. Cl.
CPC .... *A61F 13/55145* (2013.01); *A61F 13/5514* (2013.01)

(58) Field of Classification Search
CPC .... A61F 15/001; A61F 15/003; A61F 13/551; A61F 13/55135; A61F 13/5519; A61F 13/5513; A61F 13/55145; A61F 13/5514; B65D 2251/0021; B65D 2251/0084
USPC ... 206/38, 37, 494, 235, 438, 440, 441, 570, 206/581, 233; 604/385.27; 220/259.2, 220/826
See application file for complete search history.

(56) References Cited

U.S. PATENT DOCUMENTS

| | | | | |
|---|---|---|---|---|
| 415,457 A * | 11/1889 | Hart | A45C 11/18 312/61 |
| 646,726 A * | 4/1900 | Chelimer | A45C 11/24 206/39.6 |
| 1,014,543 A * | 1/1912 | Walsh | A24F 15/18 206/92 |
| 1,342,178 A * | 6/1920 | Miller | A24F 15/18 132/297 |
| 2,112,539 A * | 3/1938 | Magnus | A45C 11/008 132/316 |
| 4,674,635 A * | 6/1987 | Huldin | B65D 83/08 206/499 |
| 4,892,188 A * | 1/1990 | Meadows | A61F 6/005 206/223 |
| 4,941,226 A * | 7/1990 | Kemper | A45D 34/04 15/104.94 |
| 5,401,093 A * | 3/1995 | Resnick | A47B 67/02 220/259.2 |
| 7,841,488 B2 * | 11/2010 | Hagihara | B65D 83/087 221/36 |
| 8,863,793 B2 * | 10/2014 | Black | A45C 1/06 150/147 |
| 2006/0266663 A1* | 11/2006 | Rhea | A45C 11/008 206/223 |
| 2015/0173573 A1* | 6/2015 | Dunn | B65D 43/16 206/581 |
| 2016/0175173 A1* | 6/2016 | Higgs-Jackson | A61F 15/001 29/434 |

* cited by examiner

*Primary Examiner* — J. Gregory Pickett
*Assistant Examiner* — Jenine Pagan
(74) *Attorney, Agent, or Firm* — Dunlap Bennett & Ludwig, PLLC; Anna L. Kinney

(57) ABSTRACT

A method and apparatus for storing a feminine hygiene article wherein one or more such feminine hygiene articles are received into a container. A feminine hygiene article is then restricted from forward movement so that one or more feminine hygiene articles are not accidentally discharged from container.

15 Claims, 10 Drawing Sheets

METHOD AND APPARATUS FOR STORING A FEMININE HYGIENE ARTICLE

BACKGROUND

Women around the globe share a common plight; that being the pain and frustration they suffer during menstruation. Modernly, many feminine hygiene products help ease the burden associated with a woman's monthly cycle. Most importantly, today's feminine hygiene products, which are also referred to herein as "articles", are substantially sterile. These products, which range from sanitary pads to tampons, are typically packaged with the notion of "single use" in mind. Hence, even though these products may be packaged in bulk for consumers, the sterile nature of the product is preserved by individually packaging each sanitary pad or tampon.

Such individually packaged feminine hygiene products offer convenience. A woman is able to carry a supply of such individually packaged feminine hygiene articles in their purse or other tote. And individually packaged feminine hygiene articles give women the confidence that their feminine hygiene products are sterile and free of contaminants.

However, individually packaging a feminine hygiene article does not necessarily prevent inadvertent contamination of the product. For example, the packaging used is easily torn, especially in an uncontrolled environment. Further, upon use, a purse is simply not a convenient means for storing the feminine hygiene articles. This is especially true in a public restroom setting where unsanitary conditions abound.

BRIEF DESCRIPTION OF THE DRAWINGS

Several alternative embodiments will hereinafter be described in conjunction with the appended drawings and figures, wherein like numerals denote like elements, and in which.

DETAILED DESCRIPTION

In the interest of clarity, several example alternative methods are described in plain language. Such plain language descriptions of the various steps included in a particular method allow for easier comprehension and a more fluid description of a claimed method and its application. Accordingly, specific method steps are identified by the term "step" followed by a numeric reference to a flow diagram presented in the figures, e.g. (step 5). All such method "steps" are intended to be included in an open-ended enumeration of steps included in a particular claimed method. For example, the phrase "according to this example method, the item is processed using A" is to be given the meaning of "the present method includes step A, which is used to process the item". All variations of such natural language descriptions of method steps are to be afforded this same open-ended enumeration of a step included in a particular claimed method.

Unless specifically taught to the contrary, method steps are interchangeable and specific sequences may be varied according to various alternatives contemplated. Accordingly, the claims are to be construed within such structure. Further, unless specifically taught to the contrary, method steps that include the phrase ". . . comprises at least one or more of A, B, and/or C . . . " means that the method step is to include every combination and permutation of the enumerated elements such as "only A", "only B", "only C", "A and B, but not C", "B and C, but not A", "A and C, but not B", and "A and B and C". This same claim structure is also intended to be open-ended and any such combination of the enumerated elements together with a non-enumerated element, e.g. "A and D, but not B and not C", is to fall within the scope of the claim. Given the open-ended intent of this claim language, the addition of a second element, including an additional of an enumerated element such as "2 of A", is to be included in the scope of such claim. This same intended claim structure is also applicable to apparatus and system claims.

Figure 1:
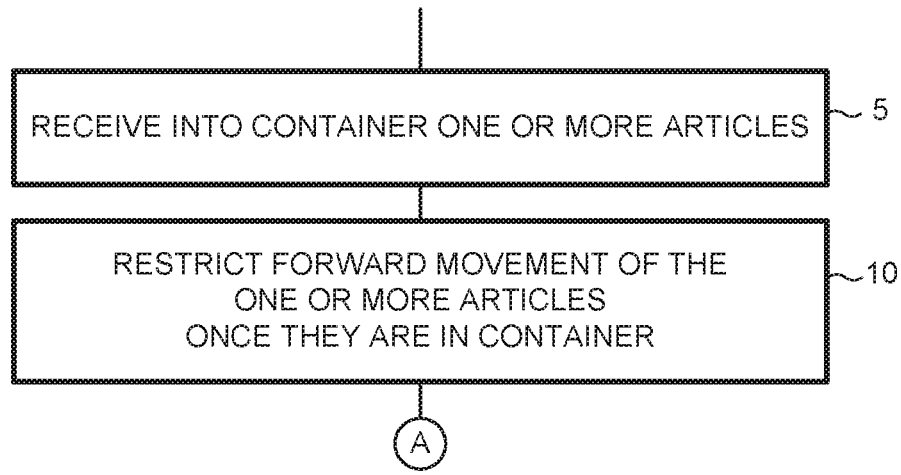
FIG. 1 is a flow diagram that depicts one example method for storing a feminine hygiene article.

FIG. 1 is a flow diagram that depicts one example method for storing a feminine hygiene article. According to this example method, a feminine hygiene article is received into a container (step 5). It should be appreciated that, according to various variations of the present method, one or more articles are received into a container. It should likewise be appreciated that, according to this example method, the forward movement of the one or more articles is substantially restricted once they are received into the container (step 10). In this way, the one or more feminine hygiene articles are less likely to be inadvertently ejected from the container.

Figure 2:
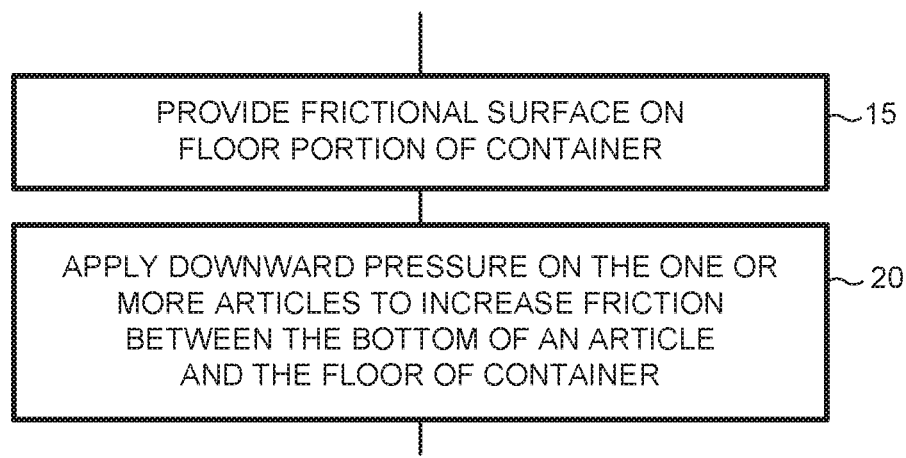
FIG. 2 is a flow diagram that depicts one alternative example method wherein the forward movement of the one or more feminine hygiene articles is restricted.

FIG. 2 is a flow diagram that depicts one alternative example method wherein the forward movement of the one or more feminine hygiene articles is restricted. According to this alternative example method, restricting the forward movement of the one or more articles, once they are received into the container, is accomplished by providing a frictional surface on a floor portion of the container (step 15). In order to enhance the restricting function of frictional surface, this alternative example method further includes a step for applying a downward pressure on the one or more articles (step 20). This downward pressure increases the friction between the bottom of an article and in the floor of the container, which is either lined with or has integral thereto a frictional surface.

Figure 3:
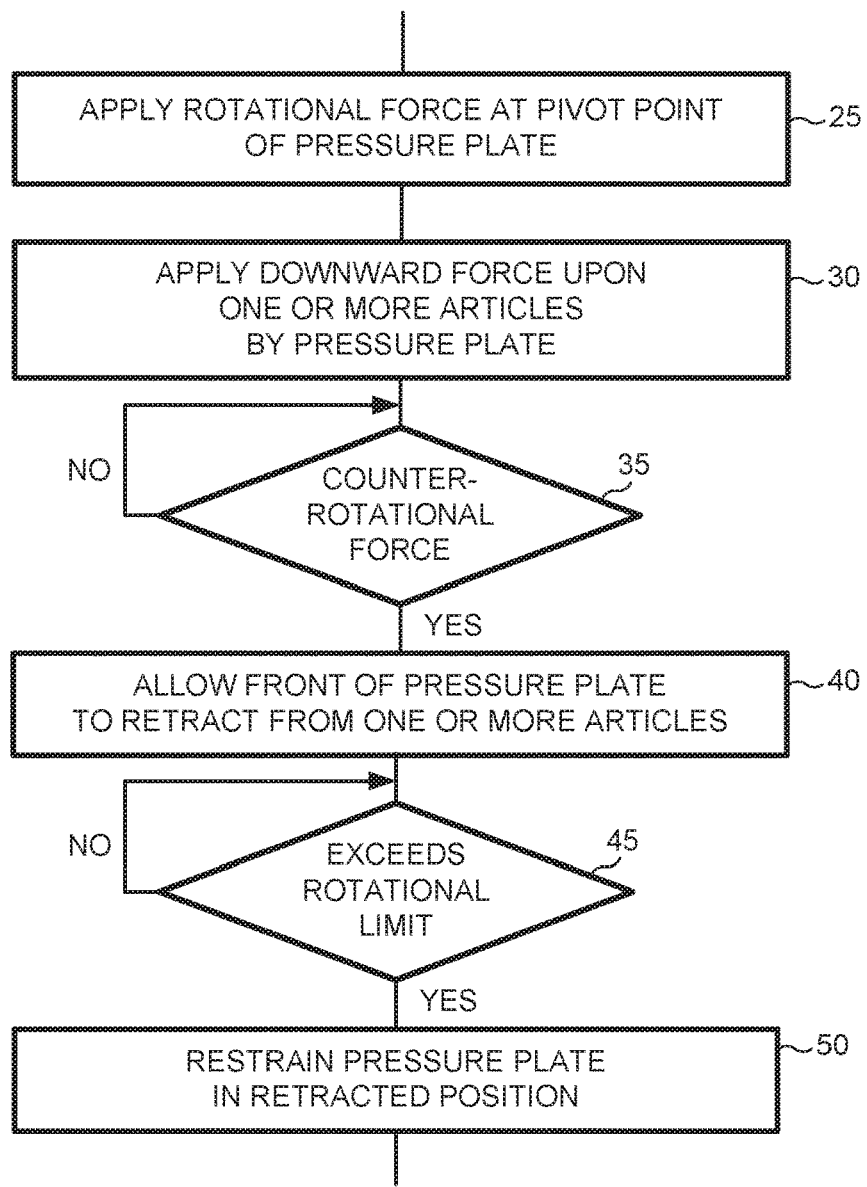
FIG. 3 is a flow diagram that depicts one alternative example method for exerting a downward force on one or more feminine hygiene articles stored in a container.

FIG. 3 is a flow diagram that depicts one alternative example method for exerting a downward force on one or more feminine hygiene articles stored in a container. According to this alternative example method, a downward force is exerted upon one or more feminine hygiene articles by applying, in an included step, a rotational force to a pivot point of a pressure plate (step 25). By applying the rotational force to a pivot point, the forward end of the pressure plate applies downward force upon the one or more articles stored in the container (step 30).

It should be appreciated that, according to one variation of this alternative example method, application of a counter rotational force (step 35) is used to retract the forward end of the pressure plate away from the one or more feminine hygiene articles (step 40) stored in the container. When the front and of the pressure plate exceeds a prescribed limit (step 45), the pressure plate is restrained in that retracted position (step 50). It should be appreciated that, according to various illustrative use cases, maintaining the pressure plate in the retracted position eases the process of storing additional feminine hygiene product articles in the container.

Figure 4:
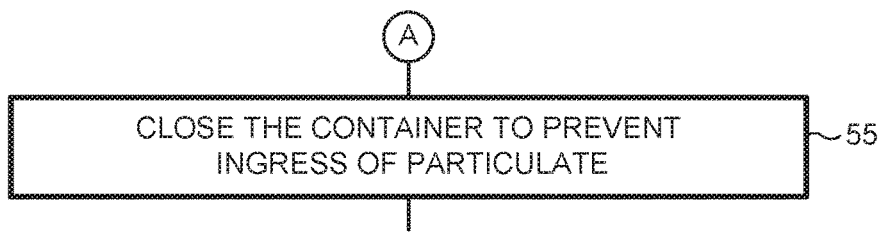
FIG. 4 is a flow diagram that depicts one alternative example method wherein the container is closed in order to prevent contamination of feminine hygiene articles stored therein.

FIG. 4 is a flow diagram that depicts one alternative example method wherein the container is closed in order to prevent contamination of feminine hygiene articles stored therein. This alternative example method further includes such step for closing the container (step 55). By closing the container, inadvertent ingress of particulate matter is substantially averted.

Figure 5:
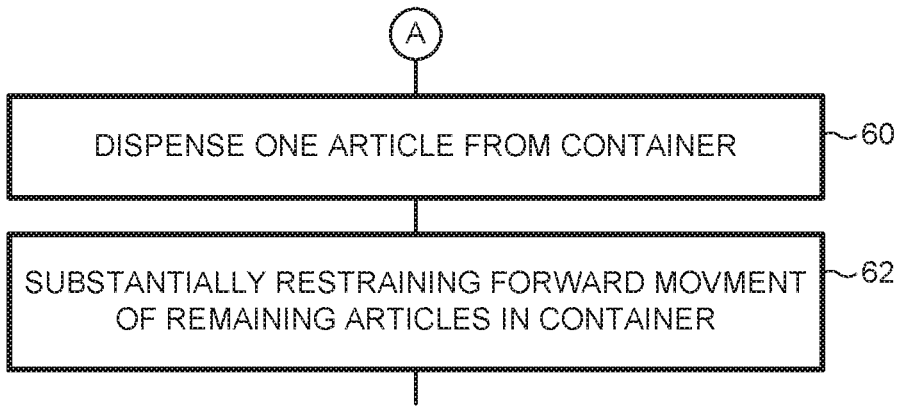
FIG. 5 is a flow diagram that depicts one alternative example method for dispensing one article from the container.

FIG. 5 is a flow diagram that depicts one alternative example method for dispensing one article from the container. This alternative example method includes a step for dispensing one article from the container (step 60) while substantially restraining the forward movement of remaining articles in the container (step 62). It should be appreciated that, according to various illustrative use cases of this alternative example method, it is beneficial to enable a user to remove a single feminine hygiene article from the container without worry that the remaining products will follow suit.

Figure 6:
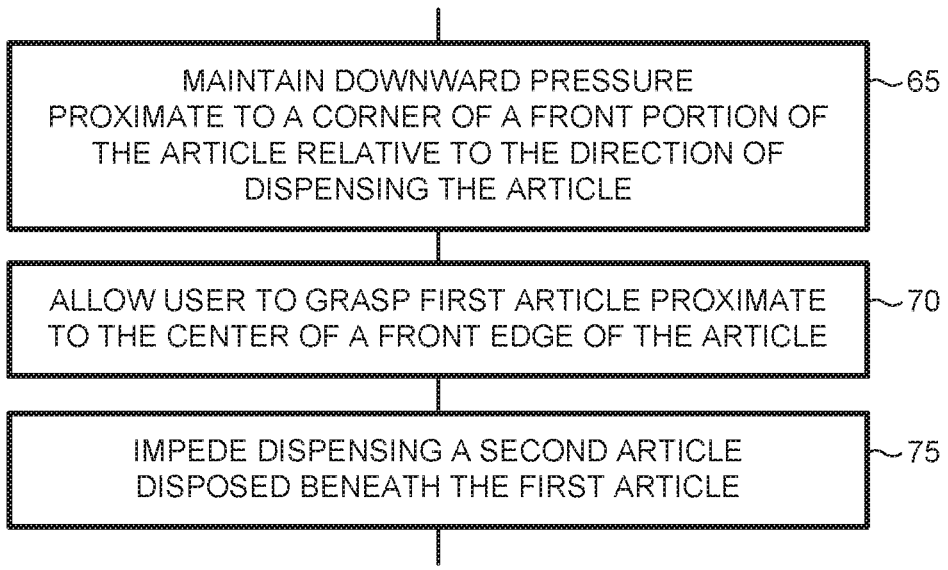
FIG. 6 is a flow diagram that depicts yet another alternative example method for dispensing one article from the container.

FIG. 6 is a flow diagram that depicts yet another alternative example method for dispensing one article from the container. In this alternative example method, downward pressure is applied upon one or more corners of a front portion of the article stored in the container (step 65). An additional included step provides for allowing the user to grasp a first article near the center of the front edge of the article (step 70). This alternative example method also includes a step for impeding the dispensation of a feminine hygiene article that is disposed immediately beneath the first article (step 75), said first article being the article to be dispensed to a user.

Figure 7:
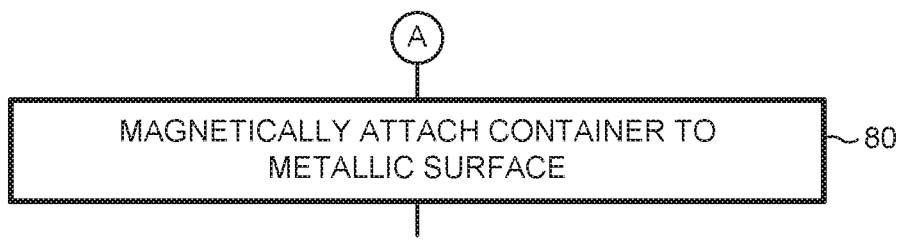
FIG. 7 is a flow diagram that depicts one alternative example method wherein the container is attached to a metallic surface.

FIG. 7 is a flow diagram that depicts one alternative example method wherein the container is attached to a metallic surface. It should be appreciated that, due to the nature of the product being stored in the container, is advantageous to temporarily attach the container to a metallic surface (step 80). It should be appreciated that, according to various illustrative use cases, the container that is used to store feminine hygiene products will be used in a public restroom setting. Accordingly, a user will find it helpful to attach the container to the side of a metallic wall, for example a partition between toilet stalls.

Figure 8:
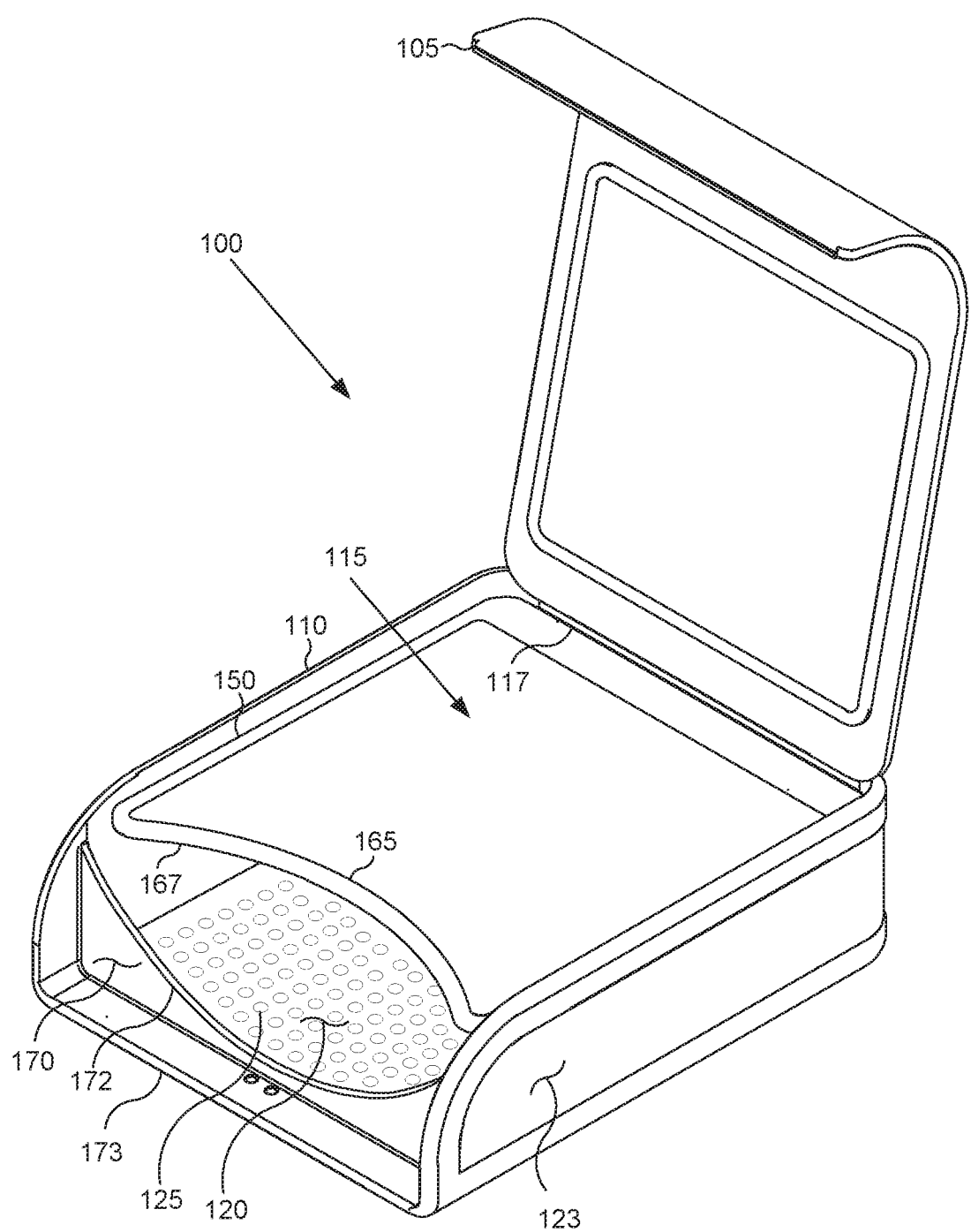
FIG. 8 is a pictorial diagram of one example embodiment of an apparatus for storing a feminine hygiene article.

FIG. 8 is a pictorial diagram of one example embodiment of an apparatus for storing a feminine hygiene article. According to this example embodiment, such an apparatus includes a container that itself includes a base portion 110 and a cover portion 105. In this example embodiment, the cover portion 105 is rotationally attached to the base portion 110 at a rear edge of the base portion 110. A retainer mechanism 115 is included in the apparatus. The retainer mechanism 115 includes a rear edge 117 and a front edge 167.

According to one alternative example embodiment, the base portion 110 includes a floor portion 120, wherein said floor portion 120 includes a frictional surface 125. According to yet another alternative example embodiment, the retainer mechanism 115 comprises a pressure plate 150 that is spring-loaded to cause the front edge 167 to rotate downward and apply a force to a floor portion 120 included in said base portion 110.

Figure 9:
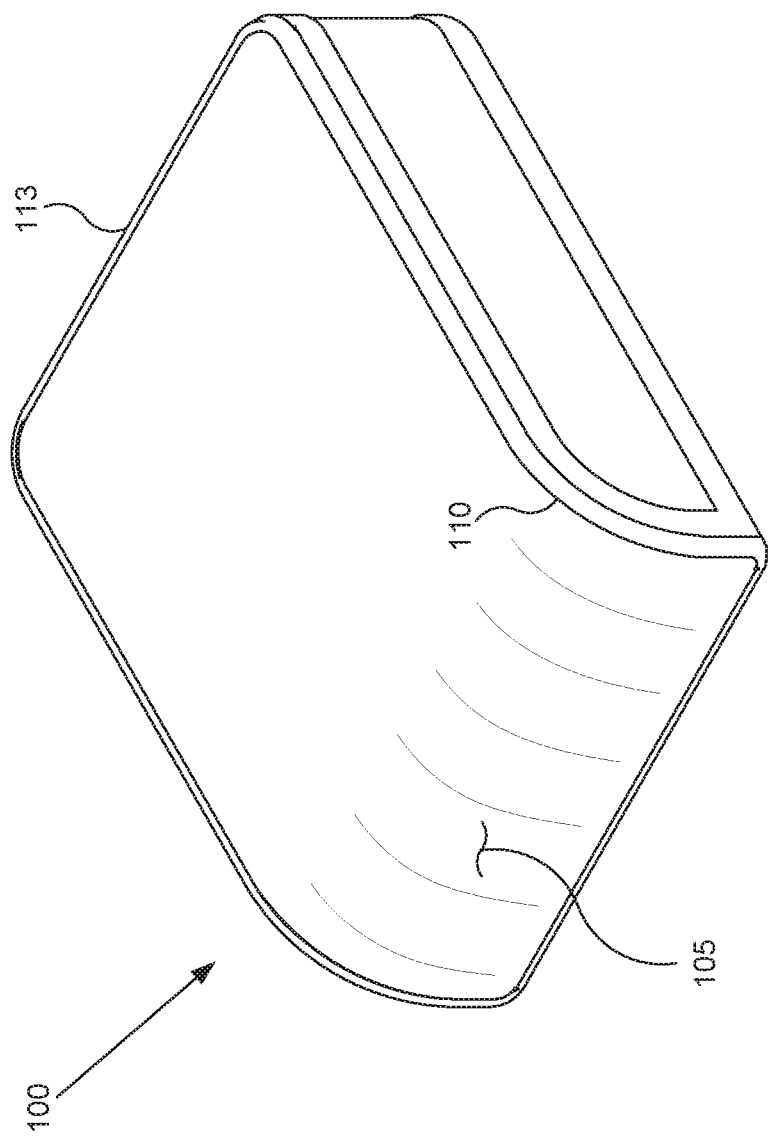
FIG. 9 is a pictorial illustration that depicts one example embodiment of an apparatus for storing a feminine hygiene article when said apparatus is fully closed.

FIG. 9 is a pictorial illustration that depicts one example embodiment of an apparatus for storing a feminine hygiene article when said apparatus is fully closed. As depicted in the figure, a base portion 110, which is included in the apparatus 100, is covered by the cover portion 105. It should likewise be appreciated that the cover portion 105 is rotationally attached to the base portion 110 at a rear edge 113 of the base portion 110. It should likewise be appreciated that, when the cover portion 105 is rotated into its closed position, the cover portion 105 of said apparatus essentially prevents ingress of particulate matter into the container portion of the apparatus 100.

Figure 10:
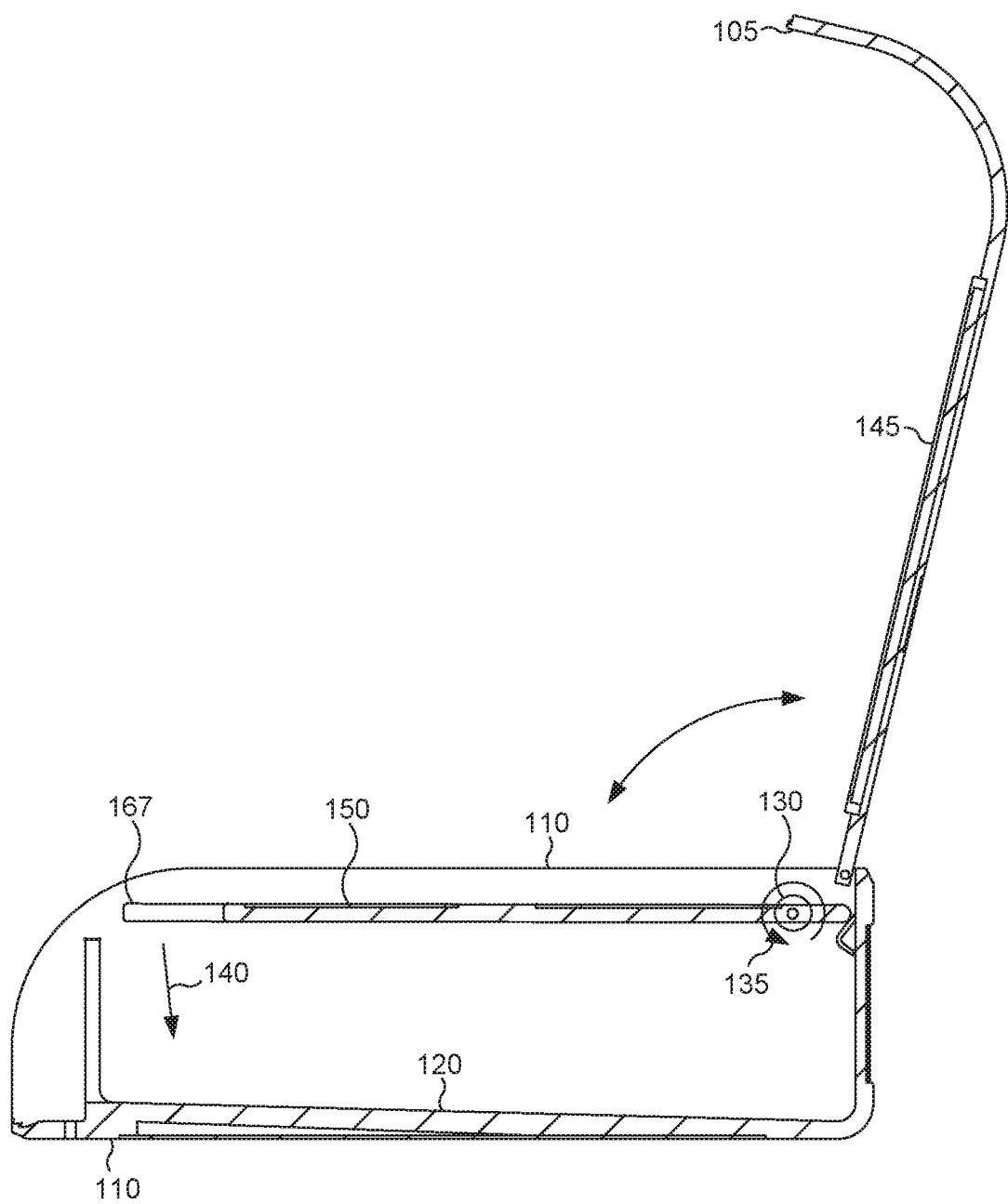
FIG. 10 is a cross-sectional view that depicts the rotational aspects of the pressure plate included in the present apparatus.

FIG. 10 is a cross-sectional view that depicts the rotational aspects of the pressure plate included in the present apparatus. As depicted in the figure, the pressure plate 150 includes a front edge 167. A torsional spring 130 is used to apply a rotational force to the pressure plate 150 proximate to its rear edge, which is defined as the edge opposite to the front edge 167. The rotational force 135 applied to the pressure plate 150 works to force the front edge of said pressure plate 150 toward 140 the floor portion 120 of the base 110. According to yet another alternative example embodiment, the cover 105 further includes a reflective surface 145 disposed on its inner surface, which may be used as a vanity mirror.

Figure 11:
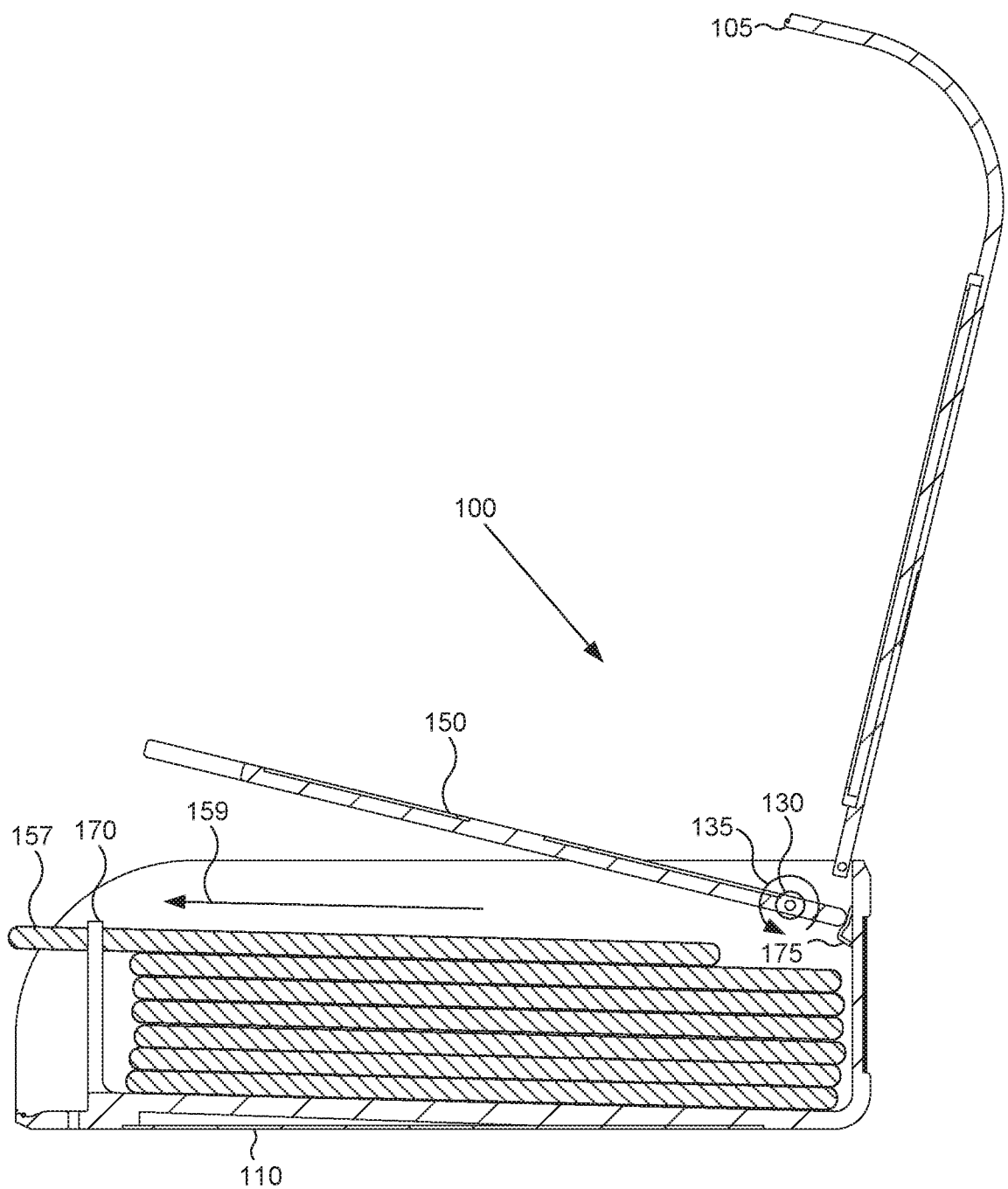
FIG. 11 is a pictorial diagram that depicts the placement of feminine hygiene articles inside the apparatus for storing such feminine hygiene articles.

FIG. 11 is a pictorial diagram that depicts the placement of feminine hygiene articles inside the apparatus for storing such feminine hygiene articles. It should be appreciated that, according to this example embodiment, feminine hygiene articles 157 are stored on the floor portion of the apparatus 100. In order to remove one such feminine hygiene article, the feminine hygiene article 157 is drawn 159 toward the front of the apparatus herein described.

FIG. 8 further illustrates that an apparatus for storing a feminine hygiene article further includes a retention wall 170, which is situated near the front edge 173 of the base portion 110 included in the apparatus 100. The retention wall 170 includes a curved recess 172. Accordingly, the retention wall 170 has a greater elevation relative to the floor portion 120 of the base 110 then it does relative to the floor portion 120 toward the center of the base 110. It should likewise be appreciated that the center of the base 110 is a region that is substantially equidistant from two rising substantially parallel side walls 123 rising from the a floor portion 120 of the base portion 110 of the apparatus. There is likewise included in the base portion 110 a rising rear wall, which is opposite to a front edge of the base portion 110.

FIG. 8 also further illustrates that the pressure plate 150 included in the retention mechanism 115 includes a front edge 167, according to one alternative example embodiment, the front edge 167 includes a curved recess section 165 proximate to the center of said front edge. It should be appreciated that the recess portion 172 of the retention wall 170 together with the recess portion 165 of the front edge 167 included in the pressure plate 150 form an egress that allows feminine hygiene articles to be extracted essentially one at a time. It should be appreciated that the egress formed by the recessed portion of the retention wall 170 and the recessed portion of the pressure plate 150 comprises a larger opening toward the center of the apparatus 100. For the sides of the apparatus 100, the egress is narrowed. Within this narrowed region of the egress, a feminine hygiene article that is not at the top of a particular stack, as shown in FIG. 11, will be substantially retained by the retention wall 170 within the container included in the apparatus 100.

Figure 12:
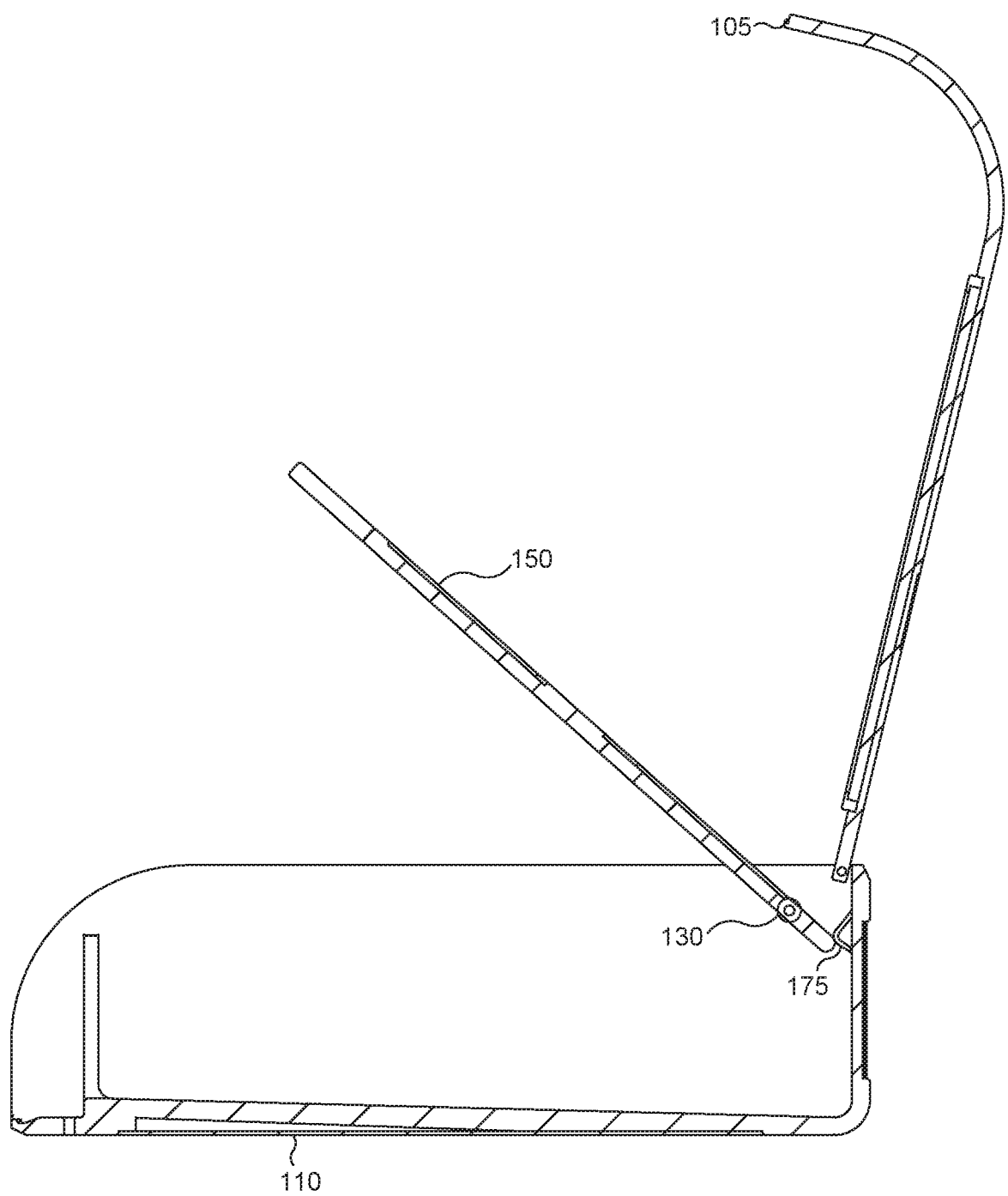
FIG. 12 is a pictorial diagram that depicts the operation of a retention ledge, which maintains a position of the pressure plate in a retracted position.

FIG. 12 is a pictorial diagram that depicts the operation of a retention ledge, which maintains a position of the pressure plate in a retracted position. According to one alternative example embodiment, the base portion 110 includes a retention ledge 175, which is disposed on an upper portion of a rear wall included in said base portion 110. According to yet another alternative example embodiment, the retention ledge 175 comprises a pliable and/or malleable material. For example, in one alternative example embodiment, the retention ledge 175 comprises a neoprene material.

FIG. 11 further illustrates that, as the pressure plate 150 is rotated against the torsional force 135, the rear edge of the pressure plate 150 begins to deform the retention ledge 175. When the pressure plate 150 is further rotated about the torsional force and 135 imparted upon the pressure plate 150 by the torsional spring 130, the retention ledge 175 regains its original shape and serves as a stop that holds the pressure plate 150 in the extracted position.

Figure 13:
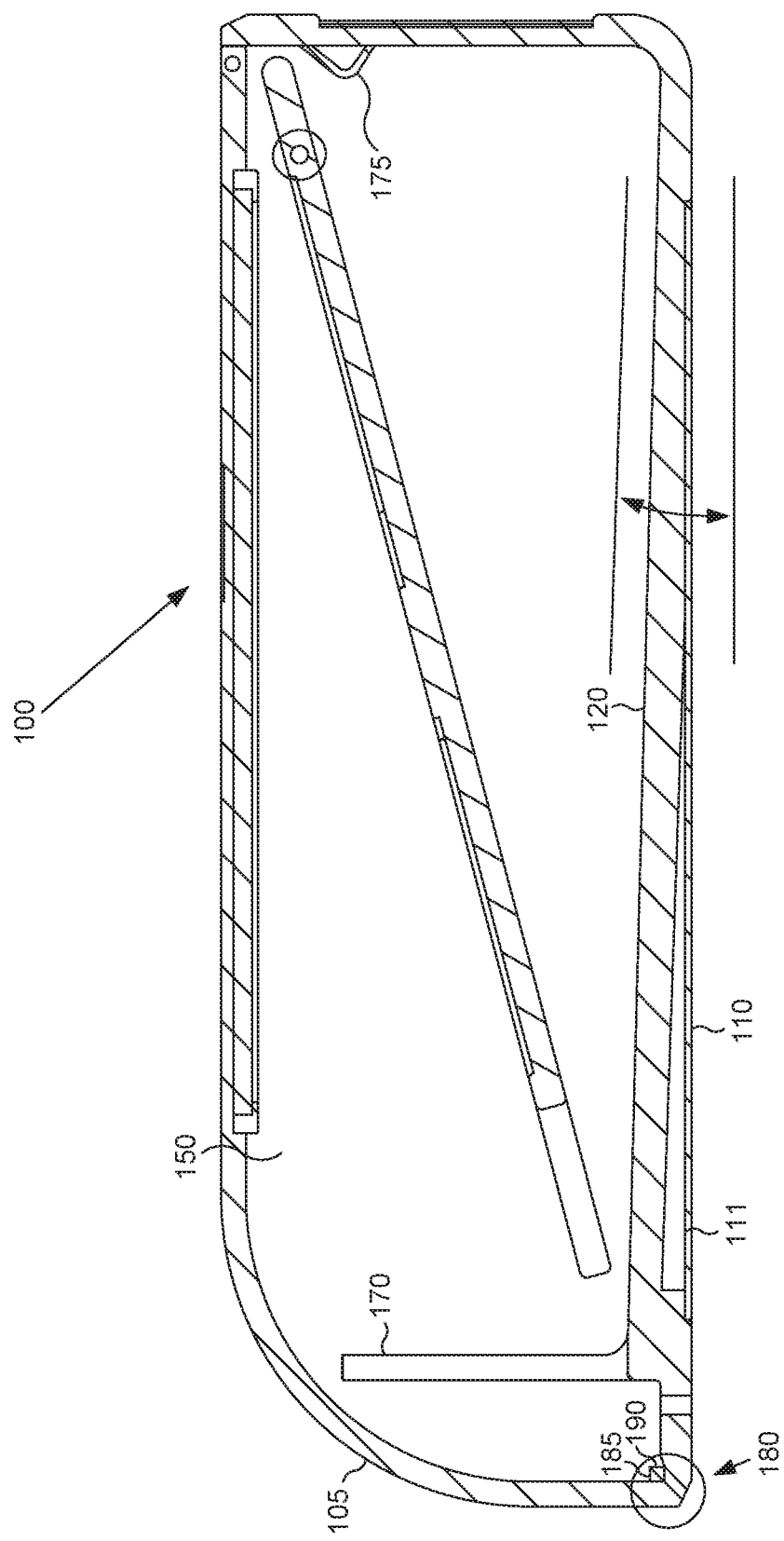
FIGS. 13 and 14 are pictorial illustrations that depict the structure of one example embodiment of a magnetic latching mechanism included in one alternative example embodiment of the apparatus herein described.
Figure 14:
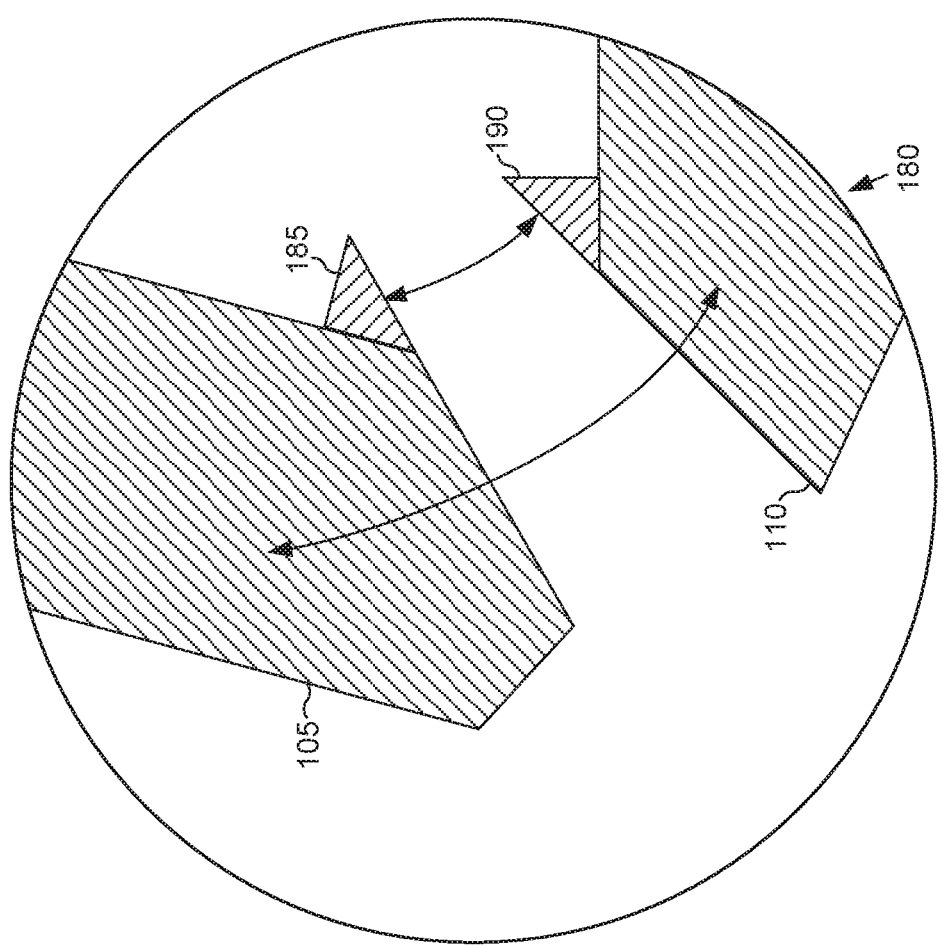

FIGS. 13 and 14 are pictorial illustrations that depict the structure of one example embodiment of a magnetic latching mechanism included in one alternative example embodiment of the apparatus herein described. According to this alternative example embodiment, the cover portion 105 includes a magnet 185 and the base portion 110 also includes a magnet 190. View 180, depicted in FIG. 14, shows that the magnet 185 included in the cover portion 105 comprises a triangular-shape as is the magnet 190 included in the base portion 110. It should be appreciated that, according to one example embodiment, the magnets include a right angle.

As depicted in the figure, the two magnets are disposed at the very inside edges of the cover portion 105 and the base portion 110. The magnets 185 and 190 are further disposed so that their hypotheses come into substantial contact with each other when the cover 105 is closed relative to the base portion 110. It should likewise be appreciated that, according to this alternative example embodiment, the triangular magnets 185 and 190 comprise strips that run a substantial portion of the inside edges of the cover portion 105 and the base portion 110 of the apparatus 100. It should likewise be appreciated that, according to this alternative example embodiment, the magnets are further postured so that the north side of one magnet juxtaposes the south side of the other magnet when the cover portion 105 is closed relative to the base portion 110.

FIG. 13 also illustrates that, according to one alternative example embodiment, the floor portion 120 of the base portion 110 where a higher elevation is presented toward the retention wall 170. FIG. 13 further illustrates that, according to one alternative example embodiment, an outer surface of the base portion 110 of the apparatus includes a cavity. In this alternative example embodiment, a piece of sheet magnet is glued into the cavity so that it presents a magnetic surface enabling the apparatus 100 to be attached to a steel wall, for example a steel wall such as a lavatory partition included in a public restroom. It should be appreciated that, according to various alternative embodiments, the sheet magnet is glued to the outer surface of the base portion 110 and need not necessarily be disposed in a cavity. Presentation of a cavity, which is included in one alternative example embodiment, provides for a flush appearance of the bottom of the apparatus 100.

While the present method and apparatus has been described in terms of several alternative and exemplary embodiments, it is contemplated that alternatives, modifications, permutations, and equivalents thereof will become apparent to those skilled in the art upon a reading of the specification and study of the drawings. It is therefore intended that the true spirit and scope of the claims appended hereto include all such alternatives, modifications, permutations, and equivalents.

What is claimed is:

1. An apparatus for storing a feminine hygiene article, comprising:
 a container including:
  a base portion having a floor portion with a rear wall and substantially parallel sidewalls rising therefrom;
  a cover portion, wherein the cover portion is rotationally attached to the substantially parallel sidewalls at a first rotational axis adjacent the rear wall, and wherein the cover portion is flush with a top edge of the rear wall when in a closed position; and
  a retainer mechanism that includes a rear-edge rotatably coupled to the substantially parallel sidewalls at a second rotational axis and a front-edge operative to-pivot substantially about the rear-edge;
  wherein the second rotational axis is spaced from the first rotational axis.

2. The apparatus of claim 1, wherein the floor portion includes a frictional surface.

3. The apparatus of claim 1, wherein the retainer mechanism comprises: a pressure plate that is spring-loaded to cause the front-edge to rotate downward and apply a force toward the floor portion.

4. The apparatus of claim 3, wherein the retainer mechanism comprises: a retention ledge that holds the pressure plate in a retracted position once the pressure plate is rotated away from the floor portion beyond a pre-established limit.

5. The apparatus of claim 1, wherein the cover portion substantially prevents ingress of particulate matter when it is rotated into a closed position.

6. The apparatus of claim 3, wherein the pressure plate has an arcuate front edge forming a recessed central region.

7. The apparatus of claim 1, wherein the floor portion slopes upward toward a front edge of said base portion.

8. The apparatus of claim 1, wherein the base portion includes a retention wall emanating upward from the floor portion opposite the rear wall; and wherein the retention wall includes an upper edge having a recessed section proximate to the center of said upper edge.

9. The apparatus of claim 1, wherein the base portion and the cover portion include front edges and further include corresponding magnet latching elements disposed proximate to their respective front edges.

10. The apparatus of claim 1, wherein the base portion includes an outer surface and further includes a magnet disposed on said outer surface.

11. The apparatus of claim 1, wherein the substantially parallel sidewalls curve downward to a front edge of the floor portion and an curved front region of the cover portion conforms to the substantially parallel sidewalls, abutting the front edge in a closed position.

12. The apparatus of claim 1, further comprising a retention wall rising from the floor portion opposite the rear wall, wherein the substantially parallel sidewalls extend beyond the retention wall.

13. An apparatus for storing a feminine hygiene article, comprising:
- a container including:
    - a base portion having a floor portion with a rear wall and substantially parallel sidewalls rising therefrom;
    - a cover portion, wherein the cover portion is rotationally attached to the substantially parallel sidewalls at a first rotational axis adjacent the rear wall; and
    - a retainer mechanism that includes a rear-edge rotatably coupled to the substantially parallel sidewalls at a second rotational axis and a front-edge operative to-pivot substantially about the rear-edge;
- wherein the second rotational axis is spaced from the first rotational axis; and
- wherein the base portion and the cover portion include front edges and further include corresponding magnet latching elements disposed proximate to their respective front edges.

14. The apparatus of claim 13, wherein the cover portion is flush with a top edge of the rear wall when in a closed position.

15. An apparatus for storing a feminine hygiene article, comprising:
- a container including:
    - a base portion having a floor portion with a rear wall and substantially parallel sidewalls rising therefrom;
    - a cover portion, wherein the cover portion is rotationally attached to the substantially parallel sidewalls at a first rotational axis adjacent the rear wall;
    - a retainer mechanism that includes a rear-edge rotatably coupled to the substantially parallel sidewalls at a second rotational axis and a front-edge operative to-pivot substantially about the rear-edge; and
    - a retention wall rising from the floor portion opposite the rear wall, wherein the substantially parallel sidewalls extend beyond the retention wall;
- wherein the second rotational axis is spaced from the first rotational axis.

* * * * *